United States Patent [19]
Doster

[11] Patent Number: 5,956,122
[45] Date of Patent: Sep. 21, 1999

[54] IRIS RECOGNITION APPARATUS AND METHOD

[75] Inventor: Rodney Doster, Garland, Tex.

[73] Assignee: Litton Systems, Inc, Woodland Hills, Calif.

[21] Appl. No.: 09/105,062

[22] Filed: Jun. 26, 1998

[51] Int. Cl.[6] ...................................................... A61B 3/14
[52] U.S. Cl. ........................................... 351/210; 382/117
[58] Field of Search ..................................... 351/205, 206, 351/207, 208, 209, 210; 382/117, 115, 128, 190; 396/18

[56] References Cited

U.S. PATENT DOCUMENTS

| | | | |
|---|---|---|---|
| 4,641,349 | 2/1987 | Flom . | |
| 5,291,560 | 3/1994 | Daugman | 351/206 |
| 5,471,542 | 11/1995 | Ragland | 351/208 |
| 5,572,596 | 11/1996 | Wildes et al. | 382/117 |
| 5,729,619 | 3/1998 | Puma | 382/115 |

*Primary Examiner*—George Manuel
*Attorney, Agent, or Firm*—Terry L. Miller

[57] ABSTRACT

An iris recognition apparatus (12*a*) and method includes a camera (22) for imaging the human retina as seen through the pupil. The reflective retina and pupil are imaged as a luminous or retro-reflective spot located in a field of view (26). A direction to the spot (i.e., the retina spot at the pupil within the iris) in the field of view is determined, and a fine-focus video camera (48) is directed along this direction to capture an image of the iris surrounding the pupil of the eye. The captured iris image can be used for unique and individual identification of the human whose eye is imaged using known data storage, retrieval, and comparison methods.

20 Claims, 5 Drawing Sheets

IRIS RECOGNITION APPARATUS AND METHOD

BACKGROUND OF THE INVENTION

1. Field of the Invention

The present invention relates to apparatus and methods for determining whether a person is recognized by reference to the eyes of this person. More particularly, the present invention relates to apparatus and methods for recognizing humans by their distinct and individual iris patterns. Most specifically, the present invention relates to an apparatus and method for determining where in a field of view the eyes of a person to be recognized are located, so that closer inspection of the eyes and of the iris of at least one of these eyes can be conducted for recognition purposes.

2. Related Technology

It is well known that humans have individual and distinct fingerprints. Methods and apparatus have been developed for identifying humans by reference to these fingerprints. Such methods of fingerprint identification have a long history, starting with entirely manual and laborious comparisons of fingerprints located at a crime scene, for example, to ink images of the fingerprints of known criminals. Understandably, such manual comparison methods are laborious and very time consuming. As the population increases, and the numbers of people with criminal records increases also, the job of finding a match between fingerprints from a crime scene and paper records of fingerprints becomes simply overwhelming. Recently, automated methods and apparatus have been developed to speed such finger print identification processes.

Similarly, it is now becoming increasingly well known that the human iris has a level and individuality and distinctiveness that exceeds even that of the human fingerprint. In the mid-1980's, Doctors Leonard Flom and Aran Safir showed that the iris is unique among individuals. These doctors patented a method of using the human iris to identify individual people, and formed a company named IriScan, which is a leader in the field of identifying people from their iris patterns. Attention is directed to U.S. Pat. No. 4,641,349, issued Feb. 3, 1987 to Drs. From and Safir.

Another worker in this field who is credited with inventing some of the current technology is Doctor John G. Daugman of the Computer Laboratory of the University of Cambridge. Attention is directed to U.S. Pat. No. 5,291,560, issued Mar. 1, 1994. This patent is believed to deal with the problem of iris pattern signal processing and correlation. However, the burden of comparing iris patterns to a data base of such patterns would be virtually impossible without the application of similar sorting technologies from fingerprint identification. Further, iris patterns are being currently treated as bar codes, the sorting and identification technology for which is already well developed.

The IriScan technology is believed to require a person who wishes to be identified to look with a selected eye through a portal. The portal leads into a machine which captures an image of the iris of the eye so presented. The Sensar Company is believed to use IriScan technology in their Sensar Secure identification system. Another system believed to by similar is offered by Oki Electric Industries Co. Ltd. Of Japan, and is known as an Iris Personal Identification System. This latter system is believed to rely upon a video camera which captures a visible light image of the subject, and a pattern recognition software which picks out the subjects face from the background image. Once the subject's face is identified in the field of view then further pattern recognition is conducted to identify and locate a selected eye on the subject's face. This location is then provided to a servo system which directs a fine-focus telephoto video camera toward the location of the person's selected eye. This fine focus video camera then captures an image of the selected eye of the subject, including the iris of this eye, for further processing into a "bar code" pattern which allows definite recognition of the subject.

In view of the above, it is easily understood that the image processing burden on an identification system is substantial in order to pick out the person's face, and the selected eye of a person, and to do this job fast enough to allow such a system to be accepted for use. For example, the systems can be used at airports for passenger identification, and at ATM machines, for example. However, the identification of the person before the machine must be performed in a matter of a few seconds, or desirably less. As can be appreciated, in the event that the pattern recognition software mistakenly directs the fine focus video camera to a location other than the selected eye of the person, the system will not capture an image of an eye it can recognize even when the subject should be recognizable to the system. This inability of the current technology to reliably and quickly locate a selected eye of a person within a field of view to be surveyed represents a serious shortcoming in the conventional technology, and one which must be overcome if iris identification systems are to receive widespread public acceptance.

SUMMARY OF THE INVENTION

In view of the above, it is an object for this invention to avoid one or more of the short comings of the related technology.

More particularly, it is an object for this invention to provide apparatus and methods for locating the iris of a human in a field of view.

Still additionally, it is an object for this invention to provide apparatus and methods for directing a camera at the location of a selected one of the human iris so located in a field of view.

Additionally, and further to the above, it is an object for this invention to provide apparatus and methods for locating human iris by directing a beam of light into a field of view, and detecting the reflection from the human retina.

Thus, according to one aspect, the present invention provides a method of locating human iris in a field of view including the steps of beaming light into the field of view, causing the beamed light to be reflected in part from the retina of a human in the field of view, and detecting the reflection of this beamed light from the retina of a person in the field of view.

According to another aspect, this invention provides apparatus for locating and identifying a human by reference to the iris pattern of the human in a field of view of the apparatus, and including a projector for beaming light into the field of view, a detector for detecting the reflection of the beamed light from the retina of a human in the field of view and producing a detection signal, processing means for determining from the detection signal the direction to the iris of the human in the field of view, and this processor providing servo signals to a servo driving a camera to align with the direction of the human iris in the field of view.

A better understanding of the present invention will be obtained from reading the following description of particularly preferred exemplary embodiments of the present invention when taken in conjunction with the appended drawing Figures, in which the same features (or features analogous in structure or function) are indicated with the same reference numeral throughout the several views. It will be understood that the appended drawing Figures and description here following relate only to one or more exemplary preferred embodiments of the invention, and as such, are not to be taken as implying a limitation on the invention. No such limitation on the invention is implied, and none is to be inferred.

BRIEF DESCRIPTION OF THE DRAWING FIGURES

FIG. 3a provides a ray-trace diagram of light entering a human eye, and being in part reflected from the retina of this eye;

DETAILED DESCRIPTION OF EXEMPLARY PREFERRED EMBODIMENTS OF THE INVENTION

Figure 1:
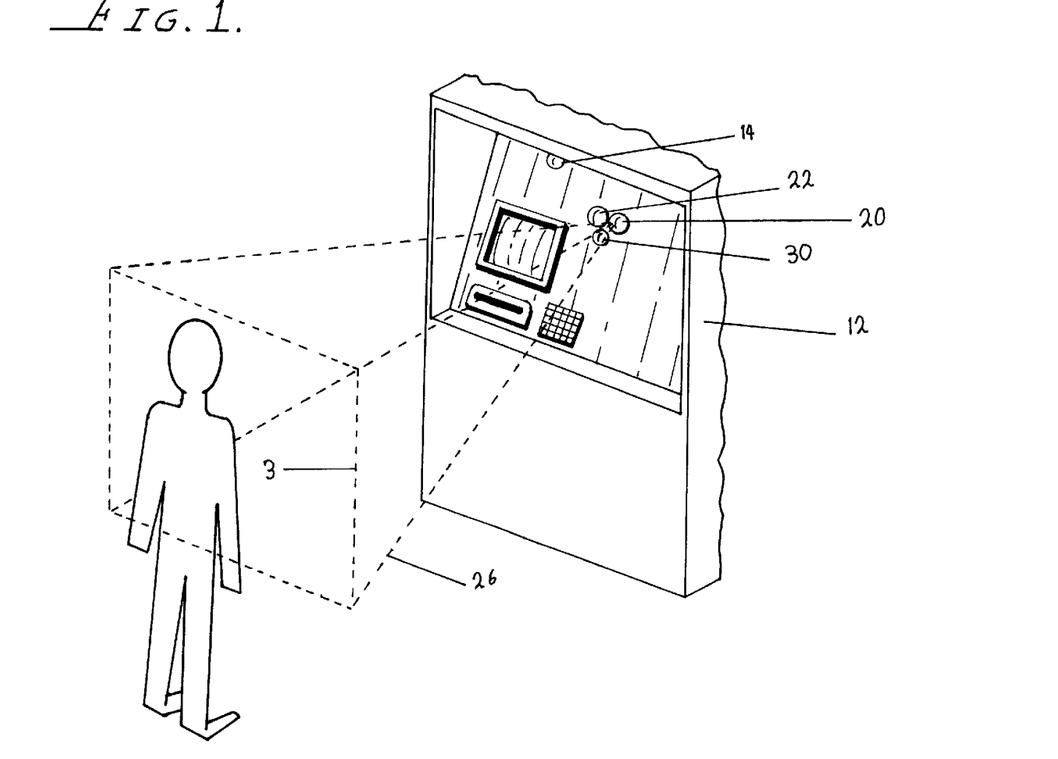
FIG. 1 provides a perspective and somewhat diagrammatic view of a human approaching a kiosk (such as a banking ATM machine) which embodies a iris recognition apparatus according to the present invention.

Viewing first FIG. 1 for an overview of the context in which the present invention may be found, it is seen that a human 10 is approaching a machine kiosk 12, which may be a bank ATM, an airline ticket dispensing machine, a security station, or another type of machine needing to recognize the people who want to use is or who pass by it, for example. It will be understood that the kiosk 12 is merely exemplary, and that apparatus 12a embodying the present invention may be utilized in contexts other than a bank ATM. For example and without limitation, the recognition apparatus 12a embodying the present invention might be utilized at an airport to identify persons who want to buy tickets, or passengers who are ticketed to board a particular aircraft, or to identify authorized airport personnel who have access to the baggage loading area or aircraft maintenance area of an airport. Other contexts in which apparatus 12a embodying the present invention might be used are industrial, government, police, or military sites where access to the site or facility is to be controlled. Such access can be controlled by reference to the identification of personnel by use of their unique and individual iris patterns.

Further considering FIG. 1, it is seen that the apparatus 12a within machine 12 includes a motion detector 14 so that the approach of the human 10 is detected. This detection of an approaching person can a greeting image to be displayed on a display screen 16 (perhaps along with an audio greeting issued from a speaker 18). Because of the greeting displayed on the screen 16 (possibly along with the audio greeting from the speaker 18) the human 10 is prompted to look toward this area of the apparatus 12a. Adjacent to the screen 16 are located both an infrared detector 20 and a visible light fine-focus video camera 22. The detector 20 and camera 22 are close together so that parallax is not significant between the points of view of these two devices.

Although not illustrated on FIG. 1, the detector 20 and camera 22 may be partially or fully concealed beneath a transparent (and possibly outwardly reflective) window of the machine 12. Thus, the human 10 may not be aware of the apparatus 12a, or of the mechanism by which the machine 12 will recognize this person.

Figure 2:
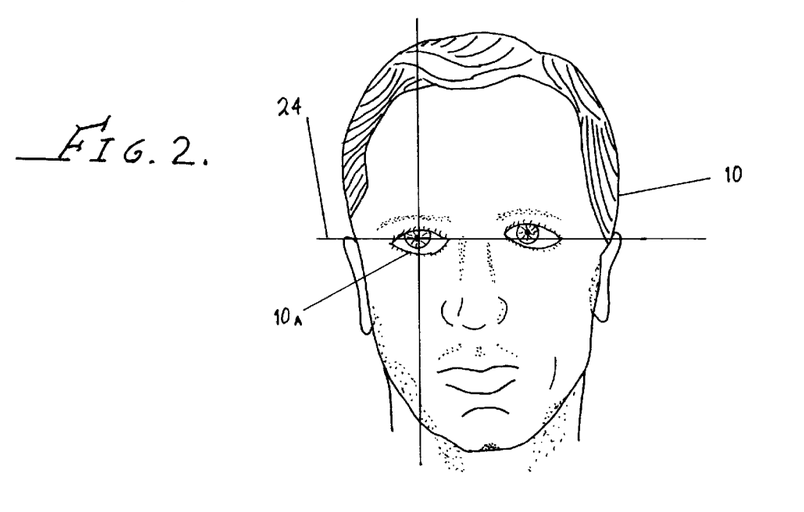
FIG. 2 is a fragmentary view of the face of the human seen in FIG. 1, but is taken from the point of view of the machine seen in FIG. 1.

Accordingly, viewing now FIG. 2, the face of the human 10 is seen from the point of view of the machine 12. It will be understood that the machine 12 does not actually obtain or detect the full facial view of the human 10 as is seen in FIG. 2, and that this drawing Figure is simply provided for purposes of explanation and better understanding of the machine 12. The human face seen in FIG. 2 has two eyes, a selected one of which is to be precisely located so that the image of the iris of this eye can be captured and converted into a somewhat circular version of a "bar code." The bar code will uniquely identify the particular person 10. In this case, the right-hand eye 10a of the person 10 has been selected for identification purposes, and a reticule pattern 24 is illustrated on FIG. 2 for reference purposes only. This reticule pattern indicates a direction to the iris of the eye 10a from the point of view of the detector 20 and video camera 22.

Figure 3:
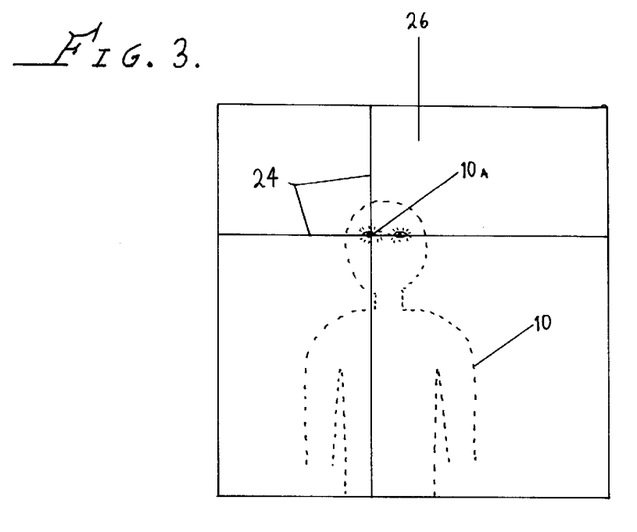
FIG. 3 is a diagrammatic representation of the face of the human and a surrounding field of view as seen in FIG. 2, and as viewed in near-infrared light.

FIG. 3 provides a representation of the image seen in near infrared light in a field of view 26 extending outwardly from detector 20 in front of machine 12. Those ordinarily skilled in the pertinent arts will understand that it is this field of view 26 which is to be surveyed by the apparatus 12a. On FIG. 1, this field of view is depicted at the approximate plane occupied by the person 10 by a dashed box indicated with the numeral 3. Those ordinarily skilled in the pertinent arts will understand that the field of view seen in FIG. 3 extends outwardly of machine 12 as a solid angle from detector 20, as is generally indicated by the dashed lines 26 of FIG. 1. As will be described, the field of view 26 has a range envelope extending from about 18 inches in front of the machine 12 to about 15 feet in front of this machine. The image seen in FIG. 3 is filtered or adjusted so that it is contrast-differentiated. That is, only features of the image having a certain contrast level above the reminder of the scene are depicted. As is seen in FIG. 3 substantially the only objects seen in this field of view above the certain contrast level are the two glowing locations of the pupils of the two eyes of the human 10.

FIG. 3a provides a diagrammatic representation of a human eye, along with a ray trace diagram of light entering this eye. The entering light is focused by the lens of the eye on the retina, and is in part reflected from this retina to be returned outwardly of the lens of the eye substantially toward its point of origin. As will be explained below, the machine 12 includes a source of near infrared light, and this light is in part reflected from the retina's of a human in order to produce the image seen in FIG. 3.

Figures 4, 5:
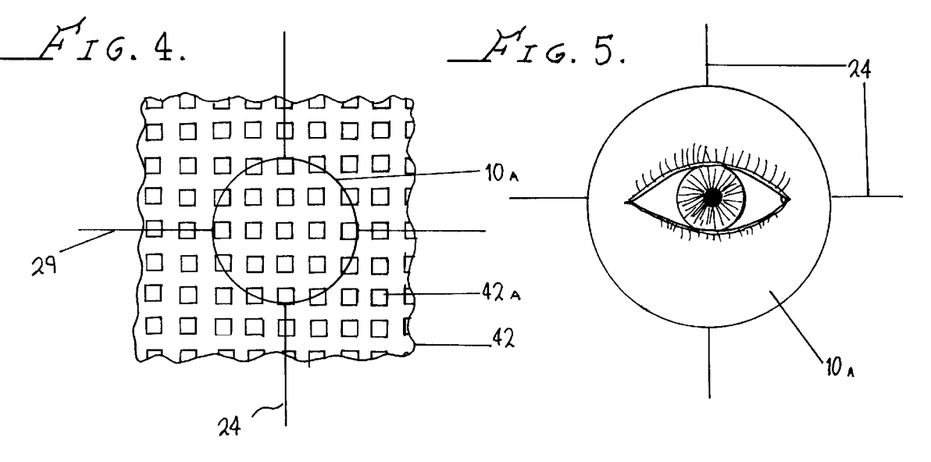
FIG. 4 provides a fragmentary and diagrammatic view of the image of a human iris as this image is produced on a component of the apparatus.
FIG. 5 is an extreme close up view of the iris of the human's right eye as seen in FIG. 2, and is presented as this iris is viewed by a visible-light video camera of the apparatus.
Figure 6:
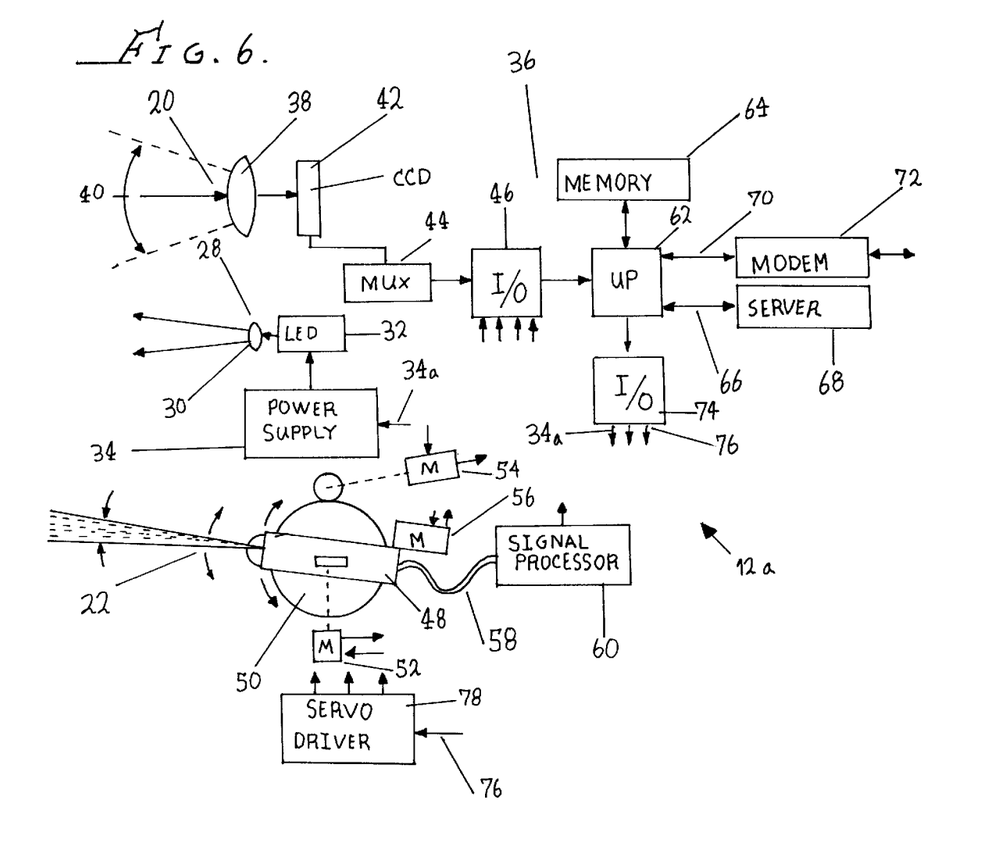
FIG. 6 is a schematic view of certain elements of the apparatus.

Viewing now FIGS. 4, 5, and 6 in conjunction with one another, and considering first of all FIG. 6 in overview, it is seen that the machine 12 includes a source of light 28, which is a source of near infrared light beamed into the field of view 26. The source of light 28 includes a lens 30 (which is also seen on the kiosk in FIG. 1), and a light emitting diode (LED) 32. The LED 32 is powered by a power supply 34, receiving a control input 34a from a control system, generally indicated with the numeral 36. In order to receive near infrared light reflected from the 25 retina of a human, and to detect the location of the pupil formed by the iris of the human's eye, the machine 12 also includes a objective lens 38 which provides a broad angle of view, indicated by the numeral 40 (which provides the field of view 26), and focuses light from this field of view onto an image capture device 42. One apparatus that may be used for image capture device 42 is a charge coupled device (CCD). As those ordinarily skilled in the pertinent arts will know, the CCD 42 includes an array of light responsive elements (commonly known as pixels). Typically these light responsive elements (i.e., the pixels) will be 200×200 or greater in resolution, for example. Another device that might be used as image capture device 42 is a CMOS image chip. In each case, the image capture device 42 will be responsive to light in the near infrared portion of the spectrum.

FIG. 4 illustrates a fragmentary view of a portion of the array of pixels 42a the CCD 42, on which the outline indicated by circle 10a indicates a group of the pixels which are illuminated by the reflected light from the eye 10a seen in FIGS. 2 and 3. The pixels 42a are in this case about 7 in number, and have a group location which is possible of determination, as will be explained. Because the location of the group of pixels illuminated within circle 10a of FIG. 4 10 is analogous to the location of the eye 10a in the field of view seen in FIG. 3, the reference location reticule 24 is also provided on FIG. 4.

A video image signal produced by CCD 42 is provided to a multiplexer 44, and subsequently is provided in multiplexed form to a input/output (I/O) interface circuit 46 of the control system 36. The I/O circuit 46 has other inputs from elements of the machine 10 as will be further described below. In order to point a high resolution narrow focus view camera 48 at the eye 10a, the machine 10 includes a gimbal mount 50 for this camera, which is moved in a horizontal plane by a servo motor 52 and in a vertical plane by a servo motor 54. Both of these servo motors receive inputs from the control circuit 36 and have position feed back outputs to this control system, each of which are indicated by the arrow symbols on FIG. 6. The outputs from the motors 52 and 54 are indicated as respective input arrows on I/O interface circuit 46. The cameral 48 similarly has a focus servo motor 56. This focus servo motor 56 also has an input from the control circuit 36, and a position feedback to this control circuit. From the video camera 48, a cable 58 provides a video signal to a video signal processor 60.

FIG. 5 illustrates that because of the position information developed at processor 60 from the image provided by CCD 42 (i.e., about the position of the eye 10a), the camera 48 is directed by action of the servo motors 52 and 54 to point at this eye. Further, the servo motor 56 is actuated to focus this camera, allowing a fine-focus close-up image of the eye 10a to be captured by camera 48. Having captured the image indicated in FIG. 5, well known software is utilized in a processor 62 having associated local memory 64 to request comparison between the captured iris image of FIG. 5 and a bank of known iris images. This comparison may be accomplished by acquiring the known iris images via a data link 66 with a local server data base computer 68. Alternatively, the known iris images may be acquired by means of a data link 70 and modem 72 giving access to a remote server data base computer (not illustrated). The processor 62 and associated memory 64 are employed to perform local operation controls of the machine 12, as is indicated by I/O circuit 74 having outputs (as are indicated by the arrows on FIG. 6), and particularly indicated by arrow 76 to a servo controller 78 for the servo motors 52, 54, and 56.

Thus, it will be understood that the microprocessor 62 performs the necessary operations to detect a pupil pair, locate a selected iris based on the location of the pupil pair, determine a direction to the selected iris, and direct the fine-focus video cameral along the determined direction to allow capture of a video image of the selected iris. After these steps are accomplished, the processor 62 may also be used locally to conduct a comparison between the captured iris image and known (i.e., known iris images), or this comparison may be handed off to a data base server computer (such as computer 68) either directly (i.e., by link 66) or by means of a remote link such as the telephone modem connection 72.

Further to the above, it will be recognized that the first embodiment of FIG. 1 employs three apertures 20, 22, and 30 in order to effect beaming of IR light into the field of view of the apparatus (via aperture 30), and recovery of an image for a wide field of view camera (via aperture 20), and for recovery of the image for the narrow field of view camera (via aperture 22).

Figure 7:
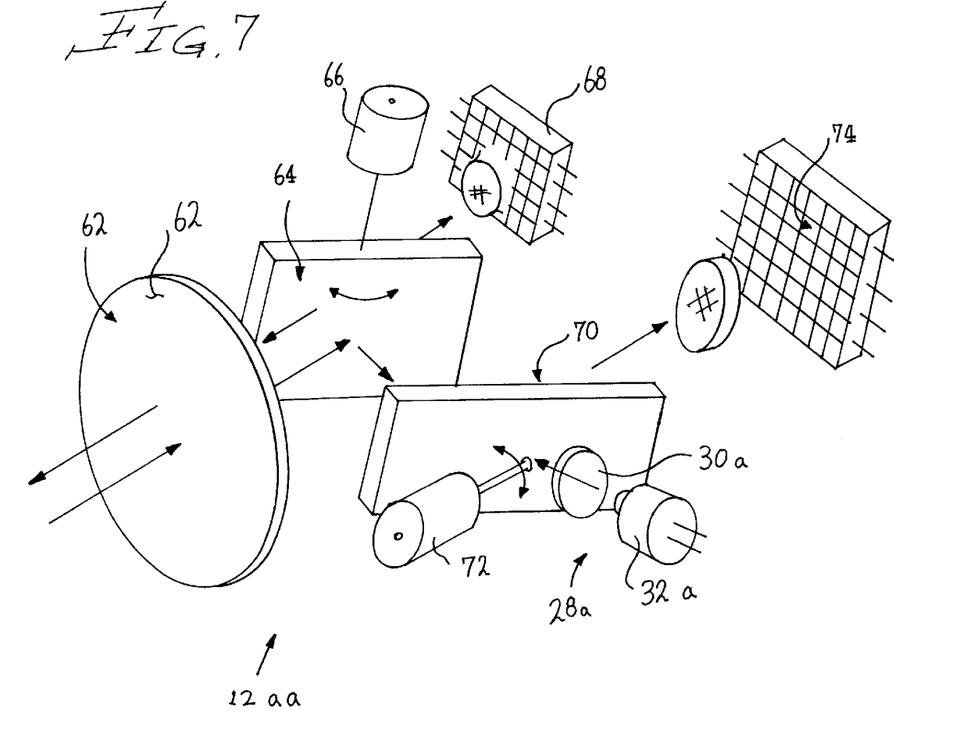
FIGS. 7 and 8 each present respective schematic illustrations of alternative embodiments of the invention.
Figure 8:
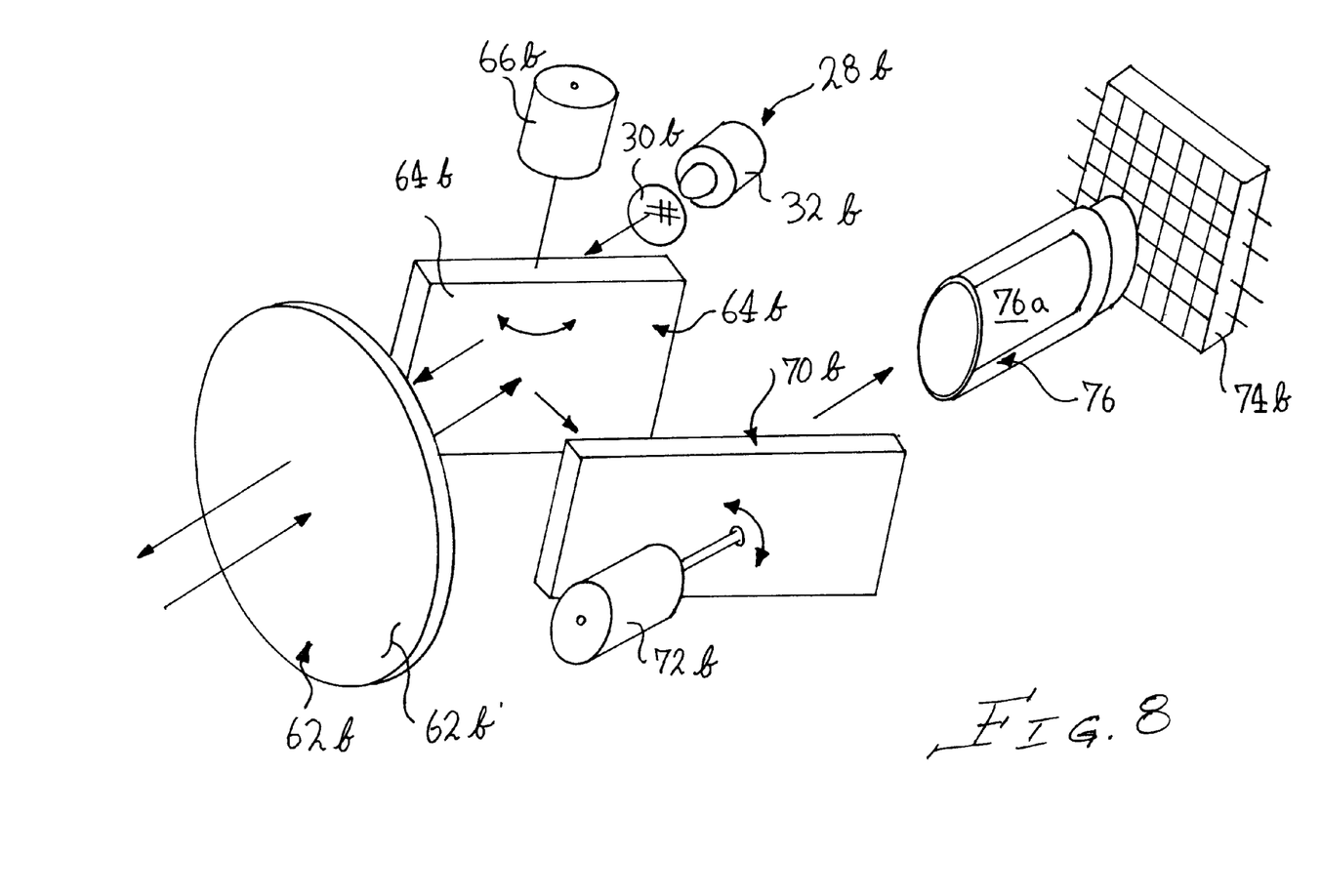

Considering now FIGS. 7 and 8, alternative embodiments of the invention are depicted. One of these embodiments reduces the number of apertures to one, while still using two cameras. The other alternative embodiment also reduces the number of apertures to one, and also reduces the number of cameras to one, although this camera is a variable-focus (i.e., zoom telephoto) type. In order to obtain reference numerals for use in describing these alternative embodiments, features of FIGS. 7 and 8 which are the same or which are analogous in structure or function to features of FIGS. 1–6 are referenced on FIGS. 7 and 8 using the same numeral used above, but with an "a" suffix added for FIG. 7, and with a "b" suffix added for the embodiment of FIG. 8.

Viewing now FIG. 7, the apparatus 12aa provides a single aperture 62 on the front of a machine (the machine is not shown in FIGS. 7 and 8, this feature having been illustrated in earlier drawing Figures). This single aperture 62 may be defined by a window member 62', which also may have spectral filter properties if desired. Behind the window 62'° is located a first scanner mirror 64, which also has beam splitter properties. In other words, the mirror 64 is both reflective and transmissive in some respects. As will be seen, both visible light and infrared light received via the window 62' are in part reflected from the scanner mirror 64, and in part are passed though this scanner mirror 64. A scanner servo 66 is drivingly connected to mirror 64 so that this mirror is controllably pivotal in a horizontal plane. Thus, the reflection from mirror 64 can be selectively scanned in a horizontal plane.

On the other hand, located behind the first scanner mirror 64 is a fixed position, fixed focus, wide field of view camera 68. Camera 68 is stationary and its view through the mirror 64 is not affected by the selective pivoting of this mirror so that an image in both the visible light and in the near-infrared light portions of the spectrum can be captured by camera 68.

Disposed to receive reflected light from mirror 64 is a second scanner mirror 70. The scanner mirror 70 is also of beam splitter type, so that a portion of the light reflected to this mirror from mirror 64 passes through the mirror 70, and another portion is reflected from the mirror 70. Mirror 70 is also associated with a scanner servo 72 so that the reflection from this mirror can be selectively scanned in a vertical plane. Located behind the mirror 70 (with respect to light reflected toward this mirror from mirror 64, is a light source 28a. This light source 28a may be provided by a light emitting diode 32a. Associated with the LED 32a is a lens 30a, which spreads the light from this LED in both the vertical and horizontal planes. Some light from this light emitting diode 32a passes through the mirror 70, and is reflected from the mirror 64. Because of the lens 30a, the light from LED 32a is sufficiently dispersed that it covers the entire field of view of the camera 68 regardless of the angular position of scanner mirror 64.

Disposed to receive light reflected from the second scanner mirror 70 is a fixed position, fixed focus, narrow field of view (i.e., telephoto) camera 74. Camera 74 is capable of capturing an image in at least the visible light portion of the spectrum. The apparatus of FIG. 7 is associated with a control system like that seen at numeral 36 of FIG. 6.

Having observed the general construction of the embodiment of FIG. 7, attention may now be directed to its operation. As can be appreciated, the LED 32a provides infrared illumination of the field of view in front of the kiosk or other machine with which the apparatus of FIG. 7 is utilized. This light is projected outwardly through aperture 62. Some of the IR light is reflected from the retinas of any person in the field of view of the apparatus which also has this apparatus in their field of view, and is returned via aperture 62 as well. This reflected light allows the location of the irises of this person to be "seen" by camera 68 (recalling the image of FIG. 3). In response to this image of the irises of the person (actually an image of the light reflected from the person's retinas seen through the irises), the control system associated with camera 68 is able to control scanners 64/66 and 70/72 so that the image of the selected one of these reflections is directed to camera 74. The camera 74 is of telephoto and fixed narrow field of view type, and captures a visible light image of the iris surrounding the illuminated retina seen through this iris. In this way an image of the selected iris can be captures for recognition purposes.

FIG. 8 presents another alternative embodiment of the invention, which also requires only a single aperture into the field of view to be surveyed. The apparatus 12ab of FIG. 8 bears some similarities to that of FIG. 7, so that similar features are referenced with the same numeral having a "b" suffix added, as was explained above. FIG. 8 shows that apparatus 12ab includes a single window 62b defining a single aperture 62b', behind which is located a scanner mirror 64b moved by a scanning servo 66b. Mirror 64b reflects light received via aperture 62b toward a scanner mirror 70b which is moved pivotally by a scanner servo 72b. Mirror 64b also allows light from a near infrared light source 28b to be beamed into the field of view of the apparatus via aperture 62b. The light originates from a near infrared LED 32b, and is dispersed by lens 30b.

Light received from the field of view of the apparatus via aperture 62b, and reflected from mirrors 64b and 70b, is directed toward a singular camera 74b. However, in this instance the camera 74b is associated with a zoom telephoto lens 76 and is responsive to light both in the visible and in the near infrared portions of the spectrum. The lens 76 has a servo 76a under control of the control system 36 (again, not shown in FIG. 8) so that the field of view of this camera 74 is selectively variable.

With the apparatus 12ab seen in FIG. 8, the control system utilizes a wide field of view of camera 74b (i.e., by setting lens 76 to a wide field of view) in order to survey the entire field of view of the apparatus in the IR portion of the spectrum to locate reflective retinas. Once a reflection is detected (and there may be several), the servos 66b, and 72b are controlled to bring a selected one of the reflections into a centered position in the field of view of camera 74. Subsequently, or simultaneously, the field of view of camera 74b is narrowed and made more telephoto by operation of servo 76a. Thus, the field of view of the camera 74b becomes narrower, and simultaneously provides a more telephoto view of the iris around the reflective retina as seen by this camera. In this way, a visible light image of the iris is obtained. By a successive process of inspecting each of the irises that happen to be within its field of view, the apparatus of FIG. 8 determines whether any of the people having these irises are recognized.

An advantage of the present invention results from its freedom from the need to use complex image pattern recognition software in order to pick out from a cluttered visible-light image that portion of the image representing a human face. The human face portion of the image is conventionally desired in order to locate the irises for recognition. Instead, as is indicated in FIG. 3, the present invention relies upon the retro-reflective nature of the human retina, and the fact that this retina can be imaged as seen through the pupil (i.e., the opening of the iris) using near infrared light. As FIG. 3 shows, the use of this imaging methodology results in a pair of human eyes being seen as two glowing spots against a field of comparatively lower brightness. These glowing spots (i.e., the retinas of the human seen through the iris pupils) are easily located in the field of view 26, and a fine-focus camera is then responsively directed along a line leading to the selected iris. In this way, the selected human iris is located and imaged for recognition.

While the present invention has been depicted, described, and is defined by reference to particularly preferred exemplary embodiments of the invention, such reference does not imply a limitation on the invention, and no such limitation is to be inferred. The invention is capable of considerable modification, alteration, and equivalents in form and function, as will occur to those ordinarily skilled in the pertinent arts. The depicted and described preferred embodiments of the invention are exemplary only, and are not exhaustive of the scope of the invention. Consequently, the invention is intended to be limited only by the spirit and scope of the appended claims, giving full cognizance to equivalents in all respects.

I claim:

1. A method of determining a direction to a human iris in a field of view, said method comprising steps of:
    beaming light into the field of view;
    causing the beamed light to be at least in part received into an eye of the human in the field of view, to be reflected from the retina, and back toward the light source via the pupil of the eye;
    detecting the part of the beamed light which is reflected from the retina; and
    determining a direction for the iris surrounding the pupil of the eye in the field of view by reference to the direction of the reflected light.

2. A method of determining a direction to a human iris in a field of view, said method comprising steps of:
    beaming light into the field of view;
    causing the beamed light to be at least in part received into an eye of the human in the field of view, to be reflected from the retina, and back toward the light source via the pupil of the eye;

detecting the part of the beamed light which is reflected from the retina; and determining a direction for the iris surrounding the pupil of the eye in the field of view by reference to the direction of the reflected light;

further including the step of utilizing infrared light as the light beamed into the field of view.

3. Apparatus for locating a human within a field of view to allow recognition of the human by reference to the iris pattern of at least one eye of the human, said apparatus comprising:

a projector for beaming light into the field of view;

a detector for detecting a part of the beamed light reflected from the retina of the human in the field of view, said detector responsively producing a detection signal;

processing means for determining from the detection signal the direction to the pupil of the human eye through which the light from the retina is reflected and of the iris of this eye surrounding the pupil; and a servo directing a line of sight for a camera into alignment with the direction to the human iris so located in the field of view;

said camera providing an image of the iris so as to image this iris; and iris pattern recognition means for utilizing the iris image to make a recognition determination.

4. Apparatus for detecting the presence and direction to a human iris in a field of view, said apparatus comprising:

a source of infrared light beamed into the field of view;

a detector responsive to reflected infrared light which is reflected from a human retina through the iris of the eye have this retina, said detector providing a response signal;

a processor receiving said response signal and determining a direction to the iris.

5. The apparatus of claim 4 wherein said apparatus further includes a servo directing a line of sight for a camera along said direction; and said camera capturing an image of the retina.

6. The apparatus of claim 4 wherein said servo includes a scanner mirror reflecting the line of sight of the camera selectively into the field of view, and said servo selectively pivots said scanner mirror.

7. The apparatus of claim 4 wherein said scanner mirror is pivotal in a first plane, and said servo further includes another scanner mirror and another servo selectively pivoting said another mirror in a second plane which is mutually perpendicular to said first plane.

8. The apparatus of claim 4 wherein said camera includes a narrow -focus camera.

9. The apparatus of claim 4 wherein said camera includes a zoom telephoto lens, said apparatus further including a servo actuating said zoom telephoto lens to change the focus of said camera.

10. A method for locating a human within a field of view to allow recognition of the human by reference to the iris pattern of at least one eye of the human, said method comprising steps of:

beaming light into the field of view;

causing at least a part of the beamed light to be reflected from the reflective retina of a human in the field of view;

employing a detector to receive a portion of said reflected light, and utilizing said detector to responsively produce a detection signal;

providing processing means for determining from the detection signal the direction to the pupil of a human eye in the field of view and of the iris of this eye; and directing a line of sight for a camera toward the human iris so located in the field of view.

11. A method for locating a human within a field of view to allow recognition of the human by reference to the iris pattern of at least one eye of the human, said method comprising steps of:

beaming light into the field of view;

causing at least a part of the beamed light to be reflected from the reflective retina of a human in the field of view;

employing a detector to receive a portion of said reflected light, and utilizing said detector to responsively produce a detection signal;

providing processing means for determining from the detection signal the direction to the pupil of a human eye in the field of view and of the iris of this eye; and directing a line of sight for a camera toward the human iris so located in the field of view;

utilizing a source of infrared light as said light beamed into the field of view; and providing a detector which is responsive to infrared light to provide said detection signal.

12. The method of claim 11 further including the steps of:

utilizing said camera to provide an image of the iris so as to image this iris; and employing iris pattern recognition means for utilizing the iris image to make a recognition determination.

13. The method of claim 11 further including the steps of:

utilizing a servo to direct a line of sight for the camera; and utilizing the camera to capture an image of the iris surrounding the reflective retina.

14. The method of claim 11 further including the step of using a movable scanner mirror to direct the line of sight of the camera in the field of view.

15. The method of claim 11 further including the step of using a zoom telephoto camera.

16. Apparatus for human recognition within a field of view, said apparatus comprising:

a source of infrared light, and means for beaming this infrared light into the field of view;

a detector for receiving infrared light reflected from the reflective retina of a human in the field of view, as this retina is visible through the pupil within an iris of the human in the field of view, said detector providing a detection signal;

means for determining from said detection signal a direction in the field of view to the iris of the human eye within the field of view;

a fine-focus camera for capturing an image of the iris in the field of view; and means for directing a line of sight of the fine-focus camera along the direction to the iris in order to capture an image of the iris.

17. A method of recognizing a human in a field of view by reference to the iris pattern of the human, said method comprising the steps of:

shining a light an eye of the human;

noting the location of a reflective retina of the eye in the field of view;

directing a fine-focus telephoto camera at the location of the reflective retina as visible through the pupil of the iris of the eye in the field of view; and utilizing the fine-focus telephoto camera to capture an image of the iris; and performing an iris pattern comparison to determine recognition for the human.

18. Single-aperture apparatus for performing human iris pattern recognition in a field of view, said apparatus comprising:

a single aperture opening to said field of view;

a source of light beaming through said single aperture into the field of view;

a detector receiving via said single aperture light reflected from a human retina in the field of view after said light has been beamed into the field of view via said single aperture, said detector responsively providing a detection signal;

a camera viewing the field of view through said single aperture; and means for directing a line of sight of the camera into the field of view in response to the detection signal in order to image a human iris providing a pupil through which said retina is visible in said field of view.

19. Apparatus for performing human iris pattern recognition in a field of view, said apparatus comprising:

a source of light beaming into the field of view;

a detector receiving said light after reflection from a human retina in the field of view and responsively providing a detection signal;

a camera viewing the field of view; and means for directing a line of sight of the camera into the field of view in response to the detection signal in order to image a human iris providing a pupil through which said retina is visible in said field of view.

20. Apparatus for recognizing a human, said apparatus comprising:

a source of light providing light in a beam which is directed toward the face and eyes of the human, light from the source of light reflecting from the retinas of the human eyes via the pupils of the eyes, which pupils are formed within the respective iris of each eye;

a camera viewing the human face and eyes from the same direction as the light is beamed, said camera having a line of sight;

a detector receiving light of from said source after reflection form the reflective retinas of the eyes and responsively providing a detection signal;

means for determining a direction to the eyes in response to the detection signal; and means for directing a line of sight of the camera along the direction to a selected one of the eyes in order to capture an image of the iris of the selected eye.

* * * * *